United States Patent

Khan et al.

[11] Patent Number: 6,102,898
[45] Date of Patent: *Aug. 15, 2000

[54] RADIATION COMPATIBLE LUBRICANT FOR MEDICAL DEVICES

[75] Inventors: Mohammad A. Khan, Sandy; David P. Hopkins, Salt Lake City, both of Utah

[73] Assignee: Becton Dickinson & Company, Franklin Lakes, N.J.

[ * ] Notice: Under 35 U.S.C. 154(b), the term of this patent shall be extended for 760 days.

[21] Appl. No.: 08/552,045

[22] Filed: Nov. 2, 1995

Related U.S. Application Data

[63] Continuation of application No. 08/294,213, Aug. 22, 1994, abandoned.

[51] Int. Cl.<sup>7</sup> ................................................. A61M 5/32
[52] U.S. Cl. ........................................... 604/265; 428/447
[58] Field of Search .................... 604/265, 266, 604/113, 406, 410; 424/401, 63; 428/447, 451, 425.5

[56] References Cited

U.S. PATENT DOCUMENTS

| | | | |
|---|---|---|---|
| 3,912,665 | 10/1975 | Spitzer | 260/2.5 E |
| 3,949,067 | 4/1976 | Gibbs | 424/73 |
| 4,459,318 | 7/1984 | Hyans | 604/265 |
| 4,643,715 | 2/1987 | Isono | 604/4 |
| 4,645,482 | 2/1987 | Yoshida | 604/408 |
| 4,720,521 | 1/1988 | Spielvogel et al. | 524/862 |
| 4,814,231 | 3/1989 | Onohara | 604/408 |
| 4,837,047 | 6/1989 | Sato | 604/408 |
| 4,838,876 | 6/1989 | Wong | 604/265 |
| 4,842,889 | 6/1989 | Hu et al. | 427/38 |
| 4,844,986 | 7/1989 | Karakelle et al. | 428/447 |
| 4,973,643 | 11/1990 | O'Lenick, Jr. | 528/15 |
| 4,994,265 | 2/1991 | White | 424/73 |
| 5,013,717 | 5/1991 | Solomon et al. | 514/56 |
| 5,026,607 | 6/1991 | Kiezulas | 428/423 |
| 5,037,419 | 8/1991 | Valentine et al. | 604/408 |
| 5,043,161 | 8/1991 | Scarpelli | 424/401 |
| 5,047,159 | 9/1991 | Zehler | 252/49.6 |
| 5,061,738 | 10/1991 | Solomon et al. | 523/100 |
| 5,071,706 | 12/1991 | Soper | 428/402.2 |
| 5,240,675 | 8/1993 | Wilk | 604/265 |
| 5,266,359 | 11/1993 | Spielvogel | 427/388.4 |
| 5,272,012 | 12/1993 | Opolski | 428/423.1 |
| 5,336,209 | 8/1994 | Porzilli | 604/307 |
| 5,338,312 | 8/1994 | Montgomery | 604/230 |
| 5,344,411 | 9/1994 | Domb et al. | 604/265 |
| 5,383,903 | 1/1995 | Totakura | 606/228 |
| 5,409,463 | 4/1995 | Thomas et al. | 604/167 |

*Primary Examiner*—Corrine McDermott
*Attorney, Agent, or Firm*—Eric M. Lee; Scott Servilla

[57] ABSTRACT

This invention relates to the use of vitamin E or its derivative, such as vitamin E acetate, with a silicone lubricant for use on a medical device. The vitamin E prevents degradation of the silicone lubricant when the medical device is irradiated for sterilization.

9 Claims, No Drawings

RADIATION COMPATIBLE LUBRICANT FOR MEDICAL DEVICES

This application is a continuation of application Ser. No. 08/294,213, filed Aug. 22, 1994 now abandoned.

BACKGROUND OF THE INVENTION

This invention relates in general to a radiation compatible lubricant for a medical device such as an intravenous (IV) catheter and introducer needle assembly.

IV catheters are designed to infuse normal intravenous solutions, including antibiotics and other drugs, into a patient. These catheters are also used to withdraw blood from the patient for normal blood-gas analysis as well as other blood work.

A sharp introducer needle must be used to puncture the skin, tissue and vein wall to provide a path for placement of the catheter in the vein. Typical IV catheters are "over-the-needle" catheters where the catheter is coaxially placed over the needle. Placement of the catheter and the introducer needle into the patient causes sharp pain to the patient. In order to facilitate insertion of the catheter and introducer needle into the vein and to minimize patient discomfort, the catheter and needle can both be lubricated. Most IV catheters are lubricated with polydimethyl siloxane silicone fluid or modified polydimethyl siloxane such as an amino-terminated, carboxy-terminated or polyether silicone copolymer.

Since IV catheters communicate with blood and tissues, these devices must be sterilized. The most commonly used method of sterilization is exposing the device to ethylene oxide. The alternative method is exposing the device to gamma rays or electron beams. Ultraviolet or x-rays may also be used. When these lubricated IV catheters are irradiated, the viscosity of the silicone fluid increases which affects the lubricity of the device. This effect is dependent upon the molecular weight of the specific silicone molecule as well as the exposure dose. For example, the viscosity of less viscous silicone fluid after irradiation may increase several fold and the material may remain as a liquid. On the other hand, a silicone fluid having a viscosity of one million centistokes may turn into a silicone rubber after it is irradiated. This characteristic will obviously have a deleterious effect on lubricity and the performance of the product.

Irradiation of the catheter also effects the polymer from which the catheter is formed. It is well known that irradiation of polymeric materials causes changes in the molecular structure. Usually these changes are destructive resulting in the degradation of molecules. Very often these degraded molecules exist initially in the form of ionic species or free radicals. If these free radicals are quenched as soon as they are formed, the net result is the lowering of the molecular weight of the polymer. If the irradiated material was in the form of a solution in certain solvents, the viscosity of the solution is greatly reduced. For example, a gel made of hydroxyethyl cellulose dissolved in water when irradiated at 2.0 to 5.0 megarads becomes a liquid as a result of losing the viscosity. If, on the other hand, the generated free radicals are not quenched, further degradation of the material, repolymerization of the polymer and even cross linking takes place. This can cause either a decrease or an increase in viscosity sometimes to the extent that gelation occurs. A good example is that of polyvinylpyrrolidone. When this polymer is irradiated in water solutions it gels to a thick mass. Whether gelation or degradation will occur after irradiation depends on the nature of the molecule and its environment. Most polymeric materials degrade after irradiation and few of them polymerize and cross-link after exposure to irradiation.

SUMMARY OF THE INVENTION

It is therefore an object of this invention to provide a lubricant for a medical device, such as an IV catheter and an introducer needle, that will not degrade when the medical device is sterilized by irradiation.

The lubricant of this invention comprises a mixture of a silicone lubricant and vitamin E or its derivatives such as vitamin E acetate.

The above and other objects of this invention will be apparent upon consideration of the following detailed description.

DETAILED DESCRIPTION OF THE INVENTION

There is ample information in the scientific literature about vitamin E as an anti-aging compound. The process of aging is related to time-dependent changes occurring in the cells and tissues. These deleterious changes are related to free radical reactions continuously occurring. These free radical reactions normally involve oxygen in mammalian systems. Since vitamin E is an antioxidant, its presence in the cells and tissues either prevents or inhibits these reactions. Thus, the aging process is slowed down. It is now believed that the life span of a healthy individual can be increased by five or more years as a result of vitamin E supplemented diets.

Incorporation of a certain concentration of vitamin E (alpha-tocopherol) or its derivative such as vitamin E acetate will inhibit the effects of irradiation by quenching the free radicals. Addition of vitamin E or its derivative stabilizes the silicone lubricant after irradiation. It is to be noted that the choice of vitamin E is based upon the fact that it is an excellent antioxidant and is a non-toxic metabolizable radiation stabilizer. Since vitamin E is an antioxidant it prevents degradation of the lubrication solution through oxidation and thus minimizes the effects of aging. Naturally occurring vitamin E, also known as alpha-tocopherol, is found in high concentrations of wheat germ, corn and soybean oils. The molecular structure of vitamin E is given below:

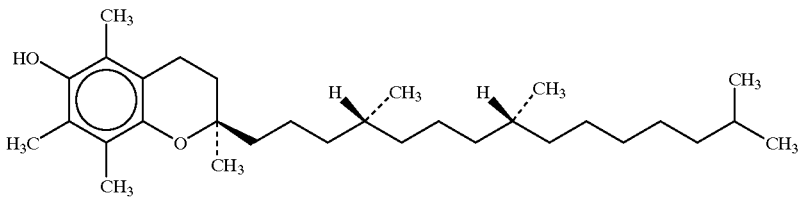

Vitamin E, or its derivative vitamin E acetate, in concentrations of between 0.5% to 20% will work according to this invention. Preferably, vitamin E or its derivative should be used in a concentration of about 2.0% to about 4.0%. Vitamin E can be used on most polymers that are used for medical devices and can be applied to all silicone based lubricants.

To demonstrate the effectiveness of vitamin E to inhibit the effects of irradiation, two series of experiments were conducted. The first series consisted of mixing vitamin E with silicone, irradiating the material and measuring the viscosity. The second series consisted of preparing the silicone lubricant with vitamin E added, dipping the catheter and introducer needle separately, and then assembling the catheters. The assemblies were irradiated and the tip adhesion was measured.

In the first series of experiments, a specified amount of vitamin E was mixed into a commercially available silicone lubricating fluid. The viscosity of the resulting mixture was measured using a Brookfield viscometer. The commercially available silicone fluids employed were (1) Dow Corning 360 polydimethyl siloxane having a viscosity of 350 centistokes (cstk), (2) Dow Corning 360 polydimethyl siloxane having a viscosity of 12,500 cstk, and (3) Union Carbide polydimethyl siloxane polyether modified Silwet 7001. The silicone vitamin E mixture was gamma irradiated and the viscosity was again measured. Some of the irradiated samples were aged at room temperature for approximately 2½ years. The viscosity of the aged samples was measured as well.

Example No. 1

| Vitamin E (%) | Silicone (%) Dow 360 (350 cstk) | Viscosity (Centipoise) 0 Mrad | 3 Mrad |
|---|---|---|---|
| 0 | 100 | 322 | 394 |
| 0.01 | 99.99 | 325 | 388 |
| 0.05 | 99.95 | 325 | 385 |
| 0.10 | 99.90 | 327 | 375 |
| 0.50 | 99.50 | 326 | 355 |
| 1.00 | 99.00 | 326 | 353 |

Example No. 2

| Vitamin E (%) | Silicone (%) Dow 360 (12,500 cstk) | Viscosity (Centipose) 0 Mrad | 3 Mrad | 3 Mrad aged 2½ years |
|---|---|---|---|---|
| 0.00 | 100.00 | 12900 | 49840 | 62000 |
| 0.50 | 99.50 | 12910 | 25880 | 26400 |
| 1.00 | 99.00 | 12930 | 23800 | 24000 |
| 1.50 | 98.50 | 12870 | 22900 | 24000 |
| 2.00 | 98.00 | 12600 | 22440 | 23200 |
| 2.50 | 97.50 | 12560 | 21600 | 22200 |
| 3.00 | 97.00 | 12560 | 21200 | 23200 |

Example No. 3

| Vitamin E (%) | Silicone (%) Union Carbide Silwet 7001 | Viscosity (Centipose) 0 Mrad | 2.6 Mrad | 5.3 Mrad | 5.3 Mrad aged 2½ years |
|---|---|---|---|---|---|
| 0 | 100 | 2300 | 2760 | 2950 | 2850 |
| 2 | 98 | 2050 | 2236 | 2300 | 2260 |
| 4 | 96 | 2100 | 2116 | 2150 | 2110 |
| 8 | 92 | 1950 | 1978 | 2000 | 2000 |
| 16 | 84 | 1850 | 1840 | 1800 | 1850 |
| 32 | 68 | 1360 | 1362 | 1350 | 1300 |

The above examples clearly demonstrate that vitamin E, if present in silicone, inhibits the increase in viscosity after the mixture is irradiated.

In the second series of experiments, silicone lubricant and vitamin E were dissolved in Freon TF. The needles and catheters, which were 20 gauge (ga), were dipped separately. The needles used dimethylsiloxane 1 MM cstk. The needles were heated at 70° C. for half an hour and then allowed to cool to room temperature. The catheters used Dow Corning 360 polydimethyl siloxane having a viscosity of 12,500 cstk. The needle and catheter assemblies were then assembled. The products were divided into two groups. The first group was retained as a control and the second group was exposed to gamma irradiation at a specified dose. These products were also aged at 60° C. and 90° C. respectively.

Example No. 4

| | Catheter Lubricant | | | | Needle Lubricant | |
|---|---|---|---|---|---|---|
| Vitamin E (%) | Vitamin E (g) | Lubricant (g) | Solvent (g) | Vitamin E (g) | Lubricant (g) | Solvent (g) |
| 0 | 0 | 3.98 | 196.02 | 0 | 4.79 | 195.21 |
| 2 | 0.081 | 3.88 | 196.04 | 0.098 | 4.82 | 195.08 |
| 4 | 0.181 | 3.84 | 196.00 | 0.192 | 4.63 | 195.17 |
| 8 | 0.325 | 3.64 | 196.04 | 0.376 | 4.46 | 195.16 |
| 16 | 0.655 | 3.39 | 196.00 | 0.762 | 4.00 | 195.24 |

These products were tested for tip adhesion.
The results are given in grams.

| | Tip Adhesion (grams) | |
|---|---|---|
| Vitamin E % | Non-irradiated | Irradiated at 2.7 Mrad |
| 0 | 241.5 (20.9) | 303.7 (43.6) |
| 2 | 212.0 (32.7) | 289.2 (15.4) |
| 4 | 222.0 (12.7) | 282.4 (35.4) |
| 8 | 214.7 (23.2) | 265.1 (15.4) |
| 16 | 234.7 (20.9) | 267.4 (15.9) |

Note: ( ) = standard deviation

The above data clearly demonstrated the ability of Vitamin E to inhibit the increase in tip adhesion of the product. The above products were aged at 90° C. for two weeks. The tip adhesion of these aged products were measured. The results are tabulated below:

| | Tip Adhesion (grams) | |
|---|---|---|
| Vitamin E % | Non-irradiated | Irradiated at 2.7 Mrad |
| 0 | 522.6 (67.2) | 577.9 (94.0) |
| 2 | 383.2 (37.7) | 495.3 (64.9) |
| 4 | 377.3 (83.1) | 528.9 (76.3) |
| 8 | 410.4 (88.1) | 521.6 (81.7) |
| 16 | 460.3 (80.3) | 565.2 (90.0) |

Note: ( ) = standard deviation

From the above data it appears that for this system 2%–4% of vitamin E in silicone fluid will provide the optimum protection. The above also shows the effect of aging and the concentration of vitamin E on tip adhesion of the product.

EXAMPLE NO. 5

In this experiment, two sets of needle lubricants were prepared. The control lubricant contained 2.4% 1 MM cstk silicone. The experimental lubricant contained 0.048% vitamin E and 2.35% 1 MM cstk silicone. The silicone in both lubricants was dissolved in Freon TF. Similarly, a control catheter lubricant contained 2.0% Dow Corning 360 (12,500 cstk) silicone. Again, the silicone in both lubricants was dissolved in Freon TF. These products were divided into three groups as follows:

Group A: non-irradiated, control and aged at 60° C. and 90° C.
Group B: irradiated at 3.0 Mrad and aged at 60° C.
Group C: irradiated at 3.0 Mrad and aged at 90° C.

The results of tip adhesion in grams at various intervals are tabulated below:

| Days in Aging, 60° C. | Group A | Group B |
|---|---|---|
| 0 | 260.6 (12.3) | 199.3 (12.3) |
| 10 | 358.2 (57.2) | 269.7 (44.5) |
| 24 | 364.6 (36.8) | 309.2 (91.7) |
| 41 | 408.1 (45.4) | 326.4 (69.9) |
| 64 | 431.3 (27.2) | 343.7 (64.0) |

Note: ( ) = standard deviation

| Days in Aging, 90° C. | Group A | Group C |
|---|---|---|
| 0 | 260.6 (12.3) | 199.3 (12.3) |
| 7 | 412.7 (59.5) | 316.4 (33.1) |
| 21 | 470.3 (67.6) | 376.4 (7.2) |
| 38 | 567.0 (103.5) | 463.5 (81.7) |
| 61 | 449.3 (115.3) | 587.0 (0.8) |

Note: ( ) = standard deviation

Again, it is very clear from the data that Vitamin E does provide inhibitory effect against the free radicals generated due to radiation and prevents the viscosity increase.

EXAMPLE NO.6

In this example, Silwet L7001 silicone surfactant, which is from a class of such compounds known as polyalkyleneoxide dimethylsiloxane copolymer manufactured by Union Carbide, was used. The compounds are water soluble and can be used as lubricants. A series of water solutions containing different amounts of Silwet L7001 and Vitamin E in water were prepared. These solutions were used to dip the needle as well as the catheter for assembling 20 ga catheter products. These products were divided into two groups. The first group were non-irradiated and the second group were irradiated at 3.3 Mrad. The catheter tip adhesion in grams was measured. The results are tabulated below:

| | Composition | | Tip Adhesion (g) before aging | |
|---|---|---|---|---|
| Vitamin E (g) | Silwet L7001 (g) | Water (g) | non-irradiated | Irradiated at 3.3 Mrad |
| 0 | 2 | 98 | 227.9 (30.4) | 236.5 (27.2) |
| 0 | 4 | 96 | 218.4 (37.7) | 119.9 (17.7) |
| 0.08 | 1.92 | 98 | 225.6 (11.4) | 227.9 (15.4) |
| 0.16 | 3.84 | 96 | 234.3 (13.2) | 228.4 (13.2) |
| 0.24 | 5.76 | 94 | 229.3 (22.7) | 237.4 (12.3) |

Note: ( ) = standard deviation

The above products were aged at 90° C. for four days. The tip adhesion in grams was again measured. The results are tabulated below:

| | Composition | | Tip Adhesion (g) before aging | |
|---|---|---|---|---|
| Vitamin E (g) | Silwet L7001 (g) | Water (g) | non-irradiated | Irradiated at 3.3 Mrad |
| 0 | 2 | 98 | 196.6 (66.7) | 414.0 (127.6) |
| 0 | 4 | 96 | 216.6 (112.6) | 361.4 (93.1) |
| 0.08 | 1.92 | 98 | 238.8 (36.32) | 239.3 (69.9) |

-continued

| Composition | | | Tip Adhesion (g) before aging | |
|---|---|---|---|---|
| Vitamin E (g) | Silwet L7001 (g) | Water (g) | non-irradiated | Irradiated at 3.3 Mrad |
| 0.16 | 3.84 | 96 | 196.6 (50.3) | 247.4 (50.8) |
| 0.24 | 5.76 | 94 | 120.8 (83.5) | 199.8 (74.0) |

Note: ( ) = standard deviation
water = deionized sterile

In this example, again, vitamin E shows that it can quench the free radicals generated due to irradiation. It also shows that because of the quenching the increase in tip adhesion is inhibited. The data also shows that the stabilization of the lubricant by vitamin E is concentration dependent.

Thus, it is seen that a lubricant is provide that will not deteriorate upon irradiation.

We claim:

1. A lubricant that does not substantially increase in viscosity after irradiation for use with a medical device, comprising a mixture of a silicone based lubricant and either vitamin E or vitamin E acetate.

2. The lubricant of claim 1 wherein the vitamin E or vitamin E acetate comprises between about 2.0% to about 4.0% of the mixture.

3. The lubricant of either claim 1 or 2 wherein the silicone based lubricant is selected from the group consisting of polydimethylsiloxane and a block copolymer polyalkylene oxide modified polydimethylsiloxane.

4. A medical device coated with a mixture of a silicone based lubricant and either vitamin E or vitamin E acetate.

5. The medical device of claim 1 wherein the vitamin E or vitamin E acetate comprises between about 2.0% to about 4.0% of the mixture.

6. The medical device of either claim 4 or 5 wherein the silicone based lubricant is selected from the group consisting of polydimethylsiloxane and a block copolymer polyalkylene oxide modified polydimethylsiloxane.

7. A method of sterilizing a medical device, comprising:

coating the medical device with a mixture of a silicone based lubricant and either vitamin E or vitamin E acetate; and irradiating the medical device.

8. The method of claim 7 wherein the vitamin E or vitamin E acetate comprises between about 2.0% to about 4.0% of the mixture.

9. The method of either claim 7 or 8 wherein the silicone based lubricant is selected from the group consisting of polydimethylsiloxane and a block copolymer polyalkylene oxide modified polydimethylsiloxane.

* * * * *